United States Patent [19]

Nagy et al.

[11] 3,978,169
[45] Aug. 31, 1976

[54] POLYOL PHOSPHATES

[75] Inventors: Georges Nagy, Montrouge; Daniel Balde, Levallous-Perret; Lucien Sobel, Paris; Ludovic Parvi, Pont de Claix (Isere), all of France

[73] Assignee: Produits Chimiques Ugine Kuhlmann, Paris, France

[22] Filed: Feb. 3, 1975

[21] Appl. No.: 546,450

Related U.S. Application Data

[63] Continuation-in-part of Ser. No. 17,353, Aug. 1, 1969, abandoned.

[52] U.S. Cl. .............................. 260/944; 260/945; 260/953; 260/951; 260/969; 260/982; 260/2.5 AJ
[51] Int. Cl.² ...................... C07F 9/11; C08J 9/00
[58] Field of Search .......... 260/944, 945, 953, 909, 260/951

[56] References Cited
UNITED STATES PATENTS

| | | | |
|---|---|---|---|
| 3,061,625 | 10/1962 | Friedman | 260/953 |
| 3,476,835 | 11/1969 | Schwachhofer et al. | 260/944 |
| 3,538,196 | 11/1970 | Bargnauckas et al. | 260/953 |

FOREIGN PATENTS OR APPLICATIONS

| | | | |
|---|---|---|---|
| 1,270,278 | 4/1972 | United Kingdom | 260/953 |

*Primary Examiner*—Anton H. Sutto
*Attorney, Agent, or Firm*—Pennie & Edmonds

[57] ABSTRACT

Novel phosphorated and halogenated alcohols and polyols having the following general formula (I):

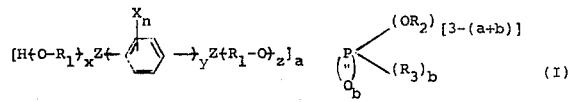

wherein:
X is a halogen atom, $R_1$ is an alkyl group of the formula (II):

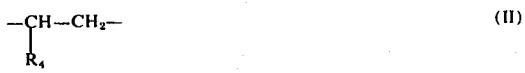

$R_4$ is a hydrogen atom, a methyl, ethyl or halomethyl group; $R_2$ is a $C_1$–$C_6$ alkyl, phenyl, $C_1$–$C_6$ alkylphenyl, phenyl ($C_1$–$C_6$ alkyl) or a halogen or hydroxy substituted $C_1$–$C_6$ alkyl, phenyl, $C_1$–$C_6$ alkylphenyl, or phenyl ($C_1$–$C_6$ alkyl) group; $R_3$ is a haloalkyl group containing from 2 to 4 carbon atoms; Z is an oxygen atom or a group

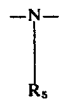

wherein $R_5$ is a hydrogen atom or a $C_1$–$C_6$ alkyl, phenyl, $C_1$–$C_6$ alkylphenyl or phenyl ($C_1$–$C_6$ alkyl) or a hydroxy substituted $C_1$–$C_6$ alkyl, phenyl, $C_1$–$C_6$ alkyl phenyl or phenyl ($C_1$–$C_6$ alkyl) group; $a$ is an integer from 1 to 3, $b$ is equal to 0 or to 1, the sum of ($a + b$) is an integer of from 1 to 3, $x$ is an integer number from 1 to 5, $y$ is an integer number from 2 to 5, $z$ is an integer number from 1 to 5 and $n$ is an integer number from 1 to 4; are prepared by transesterification of a tertiary phosphite with an alcohol or polyol.

1 Claim, No Drawings

POLYOL PHOSPHATES

REFERENCE TO RELATED APPLICATION

This is a continuation-in-part of application Ser. No. 17,353, filed on Aug. 1, 1969, presently abandoned.

SUMMARY OF INVENTION

The present invention relates to novel phosphorated and halogenated alcohols and polyols having the following general formula

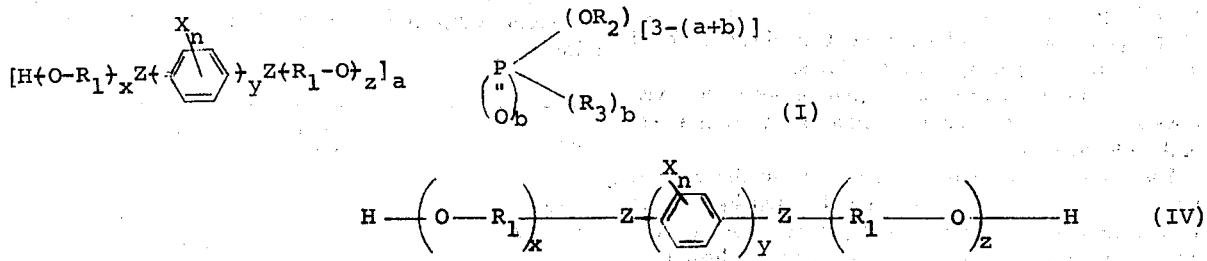

(I)

(IV)

wherein:

X is a halogen atom, $R_1$ is an alkyl group of the formula:

$$-\underset{R_4}{CH}-CH_2- \quad (II)$$

$R_4$ is a hydrogen atom, a methyl, ethyl or halomethyl group; $R_2$ is a $C_1$–$C_6$ alkyl, phenyl, $C_1$–$C_6$ alkylphenyl, phenyl($C_1$–$C_6$ alkyl) or a halogen or hydroxy substituted $C_1$–$C_6$ alkyl, phenyl, $C_1$–$C_6$ alkylphenyl or phenyl($C_1$–$C_6$ alkyl) group; $R_3$ is a haloalkyl group containing from 2 to 4 carbon atoms, Z is an oxygen atom or a group $$-\underset{R_5}{N}-$$

where $R_5$ is a hydrogen atom or a $C_1$–$C_6$ alkyl, phenyl, $C_1$–$C_6$ alkylphenyl or phenyl($C_1$–$C_6$ alkyl) or a hydroxy substituted $C_1$–$C_6$ alkyl, phenyl, $C_1$–$C_6$ alkylphenyl or phenyl($C_1$–$C_6$ alkyl) group; $a$ is an integer from 1 to 3, $b$ is equal to 0 or to 1, the sum of ($a+b$) is an integer from 1 to 3, $x$ is an integer from 1 to 5, $y$ is an integer from 2 to 5, $z$ is an integer from 1 to 5 and $n$ is an integer from 1 to 4, the method of preparing the phosphorated and halogenated alcohols and their use with other resinous materials.

The invention further includes methods of using the new alcohols or polyols and novel compositions containing the same.

DETAILED DESCRIPTION OF THE INVENTION

Generally, these products of the invention are polyols, but in the particular case wherein $R_2$ and $R_5$ do not contain a hydroxyl group and wherein $a = 1$ they are monofunctional alcohols. In the text which follows, the whole of alcohols and polyols according to the invention are designated under the word "polyols".

In other respect, the products of the invention are tertiary phosphites when $b=0$ or secondary alkylphosphonates when $b=1$.

The phosphites of this invention produced by partial or total transesterification of a tertiary phosphite having the formula $$P(OR_2)_{3-b}(OR_3)_b \quad (III)$$

wherein $b$ is equal to 0 or 1, with a polyol of the formula;

wherein X, $R_1$, $R_2$, $R_3$, Z, $x$, $y$, $z$ and $n$ have the same meaning as in the formula (I).

The compounds of the formula (IV) can be obtained by condensing a polyhalogenopolyphenyl and a polyol or an alkanolamine according to the French Pat. Nos. 1,332,697 dated June 7, 1962 and its addition, French application Ser. No. PV.120,222 of Sept. 7, 1967, and French Pat. No. 1,357,100 dated Feb. 20, 1963.

In the transesterification reaction tertiary phosphites of the formula $(R_2O)_3P$, in which $R_2$ has the same meaning as set forth in formula (I) can be used. It is preferred to employ the triphenyl phosphite or the phosphites of tri (2-chloroalkyl) obtained by the adding of three molecules of an alkylene oxide

on one molecule of phosphorous trichloride by known methods.

The transesterification is carried out by heating a mixture of the tertiary phosphite (III) and the polyol (IV), under an inert atmosphere within a range between about 100°C and 200°C (preferably between 120°C and 170°C) and removing alcohol or phenol from the reaction mixture by distillation as it forms. The process can be carried out under a normal pressure, but more often than not the use of a reduced pressure or vacuum speeds up the reaction. The reaction can be carried out in the absence or presence of a catalyst. When a catalyst is used either an alkaline catalyst, such as, sodium hydroxide, a sodium alcoholate or an alkaline metal, or a secondary phosphite $(R_2O)_2PHO$, can be used.

The transesterification is carried out with 1 to 3 moles of polyol (IV) per mole of tertiary phosphorous ester. For a molecular ratio 3 : 1, the entire transesterification leads to a tertiary phosphite complying with the formula (I) wherein $a = 3$, $b = 0$.

With lower molecular ratios, the entire transesterification can lead to linear or reticulated (cross-linked) polyphosphites, by polycondensation between the trifunctional phosphite $(R_2O)_3P$ and the polyol (IV). In order to obtain the products of the invention according to formula (I) where $b = 0$ containing the least possible polyphosphites, the transesterification should be stopped as soon as one mole of alcohol or phenol per mole of used polyol (IV) has been distilled and collected.

Tertiary phosphites corresponding to the formula (I) wherein the group $R_2$ contains free hydroxyl groups can be obtained by transesterifying alkyl, aryl or halogenated alkyl tertiary phosphites with a mixture of polyol (IV) and any other polyol. Such phosphites thus contain a greater number of free hydroxyl groups or functions.

Some examples of polyols which can be used jointly with the polyols (IV) include: glycol, glycerol, trimethylolpropane, hexanetriol-1,2,6, pentaerythrite, sorbitol and also their oxyalcoylation products.

The products obtained are liquids more or less viscous according to degree of reticulation (cross-linking) and molecular weight.

The phosphonates which correspond to the general formula (I) wherein $b = 1$ can be obtained by thermic rearrangement, according to the mechanism of the Michaelis-Arbuzov reaction, of the tertiary phosphites prepared by the partial transesterification of a mole of phosphite of tri(2-chloro alkyl) with at most two moles of polyol (IV), according to the preceding described process. The rearrangement is carried out according to the following equation.

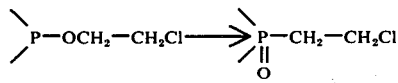

The reaction of rearrangement can be carried out under a normal pressure by heating within a temperature range between about 150°C and 220°C, and preferably between about 160°C and 180°C. The transesterification and the rearrangement reactions can also be combined in a same stage.

The phosphites according to this invention are generally vitreous, limpid, lightly colored solids which generally have a softening point under 100°C. These products are also soluble in most conventional organic solvents and in the polyether polyols or polyester polyols used for making polyurethane foams.

The new polyols and alcohols of this invention are particularly valuable for preparing plastic materials which are resistant to fire or are self-fire extinguishable. The polyols (comprising two or three hydroxyl groups or functions) are particularly useful for the preparation of polyesters and soft flexible polyurethane foams, whereas the polyols with a higher functionality are particularly useful for preparing rigid polyurethane foams. The products of this invention can be used to produce fire resistant resins and foams with the known and conventional polyesters and polyurethanes. These foams can easily be prepared by using the compounds of this invention in solutions, such as, conventional polyether polyols or polyester polyols.

The following examples illustrate specific embodiments of the present invention.

EXAMPLE 1

166 g of triethyl phosphite (1 mole), 1096 g of di(2-hydroxyethylamino)octachlorodiphenyl (2 moles) and 0.6 g of dibutyl phosphite are introduced into a flask equipped with a stirrer, a thermometer, a plunging tube and a short column Vigreux with a descending condenser and a receiver. The mixture is progressively heated under nitrogen. When the temperature reaches 100°C., the mixture is homogeneous and the ethyl alcohol begins to distill. The temperature is allowed to progressively increase up to 140°C., for 2 hours, during which 91 g of ethyl alcohol distill (1.97 moles).

The reaction mixture is then cooled and a transparent and light brown glass having a softening point approaching 80°C. is obtained. The product is a mixed phosphite of monoethyl and di(2-hydroxyethylamino-octachlorodiphenyl-aminoethyl) and analyzed as follows:

|  | Calculated | Found |
|---|---|---|
| P % | 2.65 | 2.6 |
| Cl % | 48.6 | 48.2 |
| N % | 4.78 | 4.8 |
| Acid index |  | 0.3 |
| Hydroxyl index |  | 97 (about 1.7 functions OH/kg) |

EXAMPLE II 310 g of triphenyl phosphite (1 mole) and 1,644 g of di(2-hydroxyethylamino)octachlorodiphenyl (3 moles) are introduced into the flask and apparatus described in the Example 1.

The mixture is progressively heated under nitrogen and a pressure of 20 mm Hg. The phenol begins to distill from the reaction mixture at about 90°C. The temperature is allowed to increase to 170°C. for 5 hours during which 280 g of phenol distill (2.98 moles).

The reaction is cooled and tri(2-hydroxyethylaminooctachlorodiphenylaminoethyl) phosphite is recovered which has the form of a transparent and light-brown glass having a softening point approaching 100°C. and analyzed as follows:

|  | Calculated | Found |
|---|---|---|
| P % | 1.85 | 1.82 |
| Cl % | 50.9 | 51.2 |
| N % | 5.03 | 5.1 |
| Acid index |  | 0.4 |
| Hydroxyl index |  | 100 (about 1.8 functions OH/kg) |

EXAMPLE III 311 g of tri(2-chloropropyl) phosphite (1 mole) obtained by adding 3 molecules of propylene oxide on 1 molecule of phosphorous trichloride and 1,644 g of di(2-hydroxyethylamino)octachlorodiphenyl (3 moles) are introduced into the flask and apparatus described in Example I. The mixture is progressively heated under nitrogen and under a pressure of 22 mm/Hg. A temperature of 145°C. is reached after 2 hours during which 270 g (2.85 moles) of a mixture of chloroisopropanol and chloro-2 propanol-1 are distilled from the reaction mixture (ratio about 6/1). The phosphite obtained has properties which are very similar to the products of Examples I and II and analyzed as follows:

|              | Calculated | Found |
|--------------|-----------|-------|
| P %          | 1.85      | 1.8   |
| Cl %         | 50.9      | 50.5  |
| N %          | 5.03      | 5     |
| Acid index   |           | 1.1   |
| Hydroxyl index |         | 103 (1.85 functions OH/kg) |

EXAMPLE IV 310 g of triphenyl phosphite (1 mole), 1,096 g of di(2-hydroxyethylamino)octachlorodiphenyl (2 moles) and 0.14 g of metallic sodium are introduced into the flask and apparatus described in Example I. The reaction mixture is progressively heated under nitrogen and under a pressure of 20 mm Hg. After 3 hours, the temperature reaches 145°C. and during which time 185 g of phenol (1.97 moles) are distilled off and collected. The reaction mixture is cooled down and 760 g of propoxylated sorbitol having a molecular weight of 760 is then added. The reaction mixture is again heated under 20 mm Hg, raising the temperature to 180°C. for 4 hours during which 95 g of additional phenol (1 mole) is distilled and collected. The mixed phosphite obtained is a light-brown, viscous product which flows above 50°C. and analyzed as follows:

|              | Calculated | Found |
|--------------|-----------|-------|
| P %          | 1.65      | 1.6   |
| Cl %         | 30.2      | 29.9  |
| N %          | 2.97      | 2.9   |
| Acid index   |           | 0.7   |
| Hydroxyl index |         | 210 (3.7 functions OH/kg) |

EXAMPLE V 270 g of trichloroethyl phosphite (1 mole) obtained by reacting three moles of ethylene oxide with 1 mole of phosphorous trichloride and 548 g of di(2-hydroxyethylamino)octachlorodiphenyl (1 mole) are introduced into the flask and apparatus described in Example I. The reaction mixture is progressively heated under nitrogen and under a pressure of 50 mm Hg. After 2 hours, the temperature reaches 140°C. and 80 g of glycol hydrochlorine (1 mole) distill off and is collected. The reaction mixture is cooled down and 450 g of propoxylated pentaerythrite having a molecular weight of 450 are added. The reaction mixture is again heated under 50 mm Hg, and the temperature is raised to 140°C. for 3 hours during which 79 g of glycol hydrochlorin distill off and are collected. The reaction mixture is then reduced to normal pressure and the phosphite is subjected to the rearrangement by heating under nitrogen, for 5 hours at 170°C. Further distillation of the reaction mixture under high vacuum (1 mm Hg) does not eliminate or distill any additional glycol chlorohydrin. The phosphonate (1100g) obtained is a solid product which softens at about 70°C. and analyzed as follows:

|              | Calculated | Found |
|--------------|-----------|-------|
| P %          | 2.8       | 2.6   |
| Cl %         | 28.9      | 28.3  |
| N %          | 2.53      | 2.5   |
| Acid Index   |           | 2     |
| Hydroxyl index |         | 203 (3.6 functions OH/kg) |

EXAMPLE VI 310 g of triphenyl phosphite (1 mole) and 1,914 g of p-p'bis(omega-hydroxyethoxyethyl)octachlorodiphenyl (3 moles are introduced into the flask and apparatus described in Example I. The reactiom mixture is progressively heated under nitrogen and under a pressure of 20 mm Hg. After 4 hours, the temperature reaches 175°C. and 273 g of phenol (2.9 moles) are distilled off and collected. After cooling, 1,950 g of a light-yellow vitreous solid phosphite is obtained which softens above 80°C. and which dissolves in organic solvents. The resulting product analyzed as follows:

|              | Calculated | Found |
|--------------|-----------|-------|
| P %          | 1.595     | 1.58  |
| Cl %         | 43.8      | 43.5  |
| Acid index   |           | 1     |
| Hydroxyl index |         | 90 (1.6 functions OH/kg) |

The following example describes one method of using the polyols of this invention for making rigid polyurethane foams. Similar procedures can be used for making fire retardent flexible or rigid polyester resins or polyurethane resins as will be understood by those skilled in the art.

EXAMPLE VII

Rigid polyurethane foams are prepared as follows:
The following compositions are introduced into a 500 ml stainless steel beaker and mixed by means of a stainless steel stirrer equipped with a three-bladed screw of 3 cm diameter and running at 1000 revolutions a minute:

1. A polyol obtained from any one of the preceding examples, previously dissolved in any of the non-fireproofing commercial polyols, such as listed above, (total functionality : 0.75 function OH/kg)

|    |                                 | Parts by weight |
|----|---------------------------------|-----------------|
| 2) | Silicon lubricant               | 2               |
| 3) | Diamine triethylene             | 3               |
| 4) | Stannous octoate                | 0.5             |
| 5) | Trichloromonofluoromethane      | 35 to 50        |
|    | (according to the weight of the polyol mixture) |     |

105 parts by weight of a polyphenyl isocyanate having 75 isocyanate functions/kg, are then added to the above mixture and after stirring to obtain a cream-like consistency, the mixture is rapidly poured into a mould the dimensions of which are 20 × 20 × 20 cm.

Various polyurethane foams were prepared according to the above procedure using the same components and same amounts with various amounts of the polyols of this invention and nonfireproofing polyols as listed in the table below.

The foams obtained were subjected to the fireproofing trial ASTMD 1692 59 T and results of these tests also are given in the following table:

| Fireproofing polyol | | Nonfireproofing polyol | | Assay of Foam | | | Result of the ASTM D 1692-59 T |
|---|---|---|---|---|---|---|---|
| Source | weight g | Nature | Weight g | P % | Cl % | N % | Test |
| Ex. 1 | 25 | Pentaerythrite propoxyled (9 OH/kg) | 79 | 0.26 | 4.85 | 0.48 | Self-extinguishable |
| Ex. 1 | 40 | Propoxylated pentaerythrite 9 OH/kg | 76 | 0.40 | 7.25 | 0.72 | Nonflammable |
| Ex. 2 | 25 | Propoxylated pentaerythrite (9 OH/kg) | 78 | 0.18 | 5.05 | 0.50 | Self-extinguishable |
| Ex. 3 | 60 | Propoxyled pentaerythrite (9 OH/kg) | 71 | 0.37 | 10.4 | 1.03 | Nonflammable |
| Ex. 4 | 40 | Propoxyled pentaerythrite (9 OH/kg) | 67 | 0.25 | 4.75 | 0.46 | Self-extinguishable |
| Ex. 4 | 95 | Propoxyled pentaerythrite (9 OH/kg) | 45 | 0.50 | 9.5 | 0.92 | Nonflammable |
| Ex. 5 | 25 | Propoxyled pentaerythrite (9OH/kg) | 74 | 0.26 | 2.83 | 0.25 | Self-extinguishable |
| Ex. 5 | 55 | Propoxyled pentaerythrite (9 OH/kg) | 61 | 0.51 | 5.56 | 0.48 | Nonflammable |
| Ex. 6 | 40 | Propoxyled pentaerythrite (9 OH/kg | 74 | 0.23 | 6.45 | 0 | Self-extinguishable |

The source of the particular fireproofing polyols in the above table refers to the polyols produced according to the named examples set forth above.

The above test results show that the new polyols of this invention give excellent fire resistance or fireproofing to polyurethane resins.

We claim:
1. A composition of matter comprising compounds of the general formula

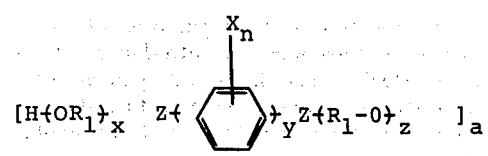

wherein X is a halogen atom, $R_1$ is an alkylene group of the formula

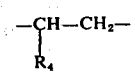

in which $R_4$ represents a hydrogen atom or a methyl, ethyl or halomethyl group; $R_2$ is an unsubstituted or halogen or hydroxyl substituted $C_1$–$C_6$ alkyl, phenyl, $C_1$–$C_6$ alkylphenyl, or phenyl($C_1$–$C_6$ alkyl) group, $R_3$ is a haloalkyl group containing from 2 to 4 carbon atoms, Z is an oxygen atom or a group of the formula

in which $R_5$ is a hydrogen atom or an unsubstituted or hydroxyl substituted $C_1$–$C_6$ alkyl, phenyl, $C_1$–$C_6$ alkylphenyl, or phenyl($C_1$–$C_6$ alkyl) group, $a$ is an integer

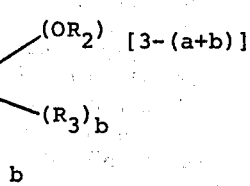

from 1 to 3; $b$ is equal to 0 or 1, provided, however, that when $a$ is 3, $b$ is 0, $x$ is an integer from 1 to 5, $y$ is an integer from 2 to 5, $z$ is an integer from 1 to 5 and $n$ is an integer from 1 to 4.

* * * * *

UNITED STATES PATENT AND TRADEMARK OFFICE
CERTIFICATE OF CORRECTION

PATENT NO. : 3,978,169
DATED : August 31, 1976
INVENTOR(S) : Georges Nagy et al.

It is certified that error appears in the above-identified patent and that said Letters Patent are hereby corrected as shown below:

Column 6, line 19 "reactiom" should be --reaction--

Column 6, line 63 "75 isocyanate" should be --7.5 isocyanate--

Signed and Sealed this

Twenty-third Day of November 1976

[SEAL]

Attest:

RUTH C. MASON
Attesting Officer

C. MARSHALL DANN
Commissioner of Patents and Trademarks